United States Patent [19]
Lormeau et al.

[11] Patent Number: 4,500,519
[45] Date of Patent: Feb. 19, 1985

[54] MUCOPOLYSACCHARIDES HAVING BIOLOGICAL PROPERTIES, PREPARATION AND METHOD OF USE

[75] Inventors: Jean-Claude Lormeau, Maromme; Maurice Petitou; Jean Choay, both of Paris, all of France

[73] Assignee: Choay S.A., Paris, France

[21] Appl. No.: 323,567

[22] Filed: Nov. 20, 1981

Related U.S. Application Data

[63] Continuation-in-part of Ser. No. 204,505, Nov. 6, 1980, which is a continuation of Ser. No. 91,164, Nov. 5, 1979, abandoned.

[30] Foreign Application Priority Data

Mar. 20, 1980 [FR] France ............................ 78 31357

[51] Int. Cl.³ ................... A61K 31/725; C08B 37/10
[52] U.S. Cl. ......................................... 514/56; 536/21; 514/822
[58] Field of Search ........................ 424/183; 536/21

[56] References Cited

U.S. PATENT DOCUMENTS

| 3,862,003 | 1/1975 | Okuyama et al. | 536/21 |
| 4,122,250 | 10/1978 | Schmer | 536/21 |
| 4,168,377 | 9/1979 | Choay et al. | 536/21 |
| 4,175,182 | 11/1979 | Schmer | 536/21 |
| 4,281,108 | 7/1981 | Fussi | 536/21 |
| 4,303,651 | 12/1981 | Lindahl et al. | 536/21 |
| 4,351,938 | 9/1982 | Barnett | 536/21 |

Primary Examiner—Johnnie R. Brown
Attorney, Agent, or Firm—Weiser & Stapler

[57] ABSTRACT

Mucopolysaccharides biologically active and more specific than heparin, particularly with respect to the blood factor Xa. These mucopolysaccharides may be obtained by partial depolymerization, under controlled conditions, of heparin, by the action of a chemical agent such as nitrous acid. The conditions implemented allow the preparation of mucopolysaccharides having a USP titer lower than that of the starting heparin and a Yin-Wessler titer at least equal to that of said heparin. These products may be used particularly as antithrombotic drugs.

42 Claims, No Drawings

MUCOPOLYSACCHARIDES HAVING BIOLOGICAL PROPERTIES, PREPARATION AND METHOD OF USE

The invention relates to mucopolysaccharide compositions having biological properties particularly the ability of more specifically controlling some steps of the blood coagulation. The invention also relates to methods for obtaining said compositions and to the use of said compositions as active principle in drugs.

The invention more particularly relates to mucopolysaccharide compositions (abbreviated herein after MPS) having a more selective activity than heparin i.e. with regard to activated factor X, or factor Xa, of the blood, and thereby a strong antithrombotic activity without haemorrhage risks for the patient.

By investigating various routes for obtaining the above-mentioned products by processes easy to put into practice and with high yields, the inventors were led to study more especially the depolymerization of haparin by the chemical route.

It will be noted that the term heparin is used in the specification and the claims in its broadest sense, in order to designate either a commercial heparin of pharmaceutical grade or a crude heparin such as obtained by extraction from biological material, particularly from mammalian tissues.

It is known that heparin produces its anticoagulant activity by protentiating the inhibitory effect of antithrombin III (or AT III) which is a plasma protein, relative to the enzymatic reactions in the course of coagulation.

As heparin is able to simultaneously depress a large number of the coagulation factors participating in the creation and the maintenance of different forms of hypercoagulability its activity does not appear specific but global.

If this anticoagulant activity turns out to be valuable, yet it makes delicate and re-equilibration of the coagulation fibrinolysis system with patients under treatment, due to the global nature of its action. It follows that the administration (for the purpose of preventing hypercoagulation risks, for example the appearance of post-surgical thromboses), of doses of an anticoagulant medicament which are too high, or the insufficient selectivity of this medicament, can finally be the cause of serious hemorrhages.

The inventors have sought MPS compositions comprising MPS chains derived from those of heparin but more satisfactory than heparin chains as regards their biological properties.

By a thorough study of various conditions for depolymerizing heparin, the inventors have found that by using specific controlled conditions, it is possible to obtain partial depolymerization of the heparin chains to a degree corresponding to the production of MPS compositions having valuable antithrombotic properties. Such MPS are capable of inhibiting the factor Xa with a degree of selectivity higher than that of heparin while their global anticoagulant activity is lower than that of heparin. Thus the ratio of the Yin-Wessler titer of these products to their USP titer is advantageous.

As is well-known, the Yin-Wessler activity is more specifically representative of the ability of the active fractions to potentiate the inhibition of the activated factor Xa of blood by the AT III in the corresponding test and the USP titer is representative of the capability of the active fractions to inhibit the total coagulation of blood or plasma.

The Yin-Wessler titer is measured by the method described by these authors in J. Lab. Clin. Med., 1976, 81, 298–300, and the USP titer is measured by the method which is described in the "Pharmacopea of the United States of America", XIX, 229–230 (see also the second supplement USP—NH, p. 62 and the fourth supplement USP—p. 90, respectively entitled "Drug Substances" and "Dosage Forms").

It is therefore an object of the invention to provide novel MPS compositions with high anti-Xa activity and having with respect to the factor Xa a remarkable selectivity within the scope of the successive enzymatic reactions which characterize the coagulation process.

It is also an object of the invention to provide a process for obtaining such kinds of products from heparin, easy to carry out on the industrial scale with high yields.

It is a further object of the invention to provide active principles of medicaments and the medicaments themselves capable notably of inhibiting the Xa factor to a high degree of selectivity whereas their activity on overall coagulation can be kept at a very low level.

The MPS compositions according to the invention are obtainable from heparin or from fractions including heparinic constituents of molecular weights ranging especially from about, 2.000 to 50.000 such as obtained by extraction from mammiferous tissues.

These compositions are characterized especially by the following points: they are soluble in a hydro-alcoholic medium (water-ethanol) having a titer of 55°–61° GL, they tend towards insolubility in a water-ethanol medium having a higher alcohol content and they are insoluble in pour alcohol. They have Yin-Wessler and USP titers respectively in a ratio equal at least to 2, notably at least 3, advantageously higher than 6, even than 10. The YW/APTT ratios are equivalent, even weaker.

The compositions, according to the present invention, are characterized also by the fact that they comprise MPS chains with end units possessing the 2,5-anhydro-D-manno basic structure of which the primary alcohol function at the 6 position is substituted or not by a —SO$_3$ group.

This terminal unit is characterized by the following general formula:

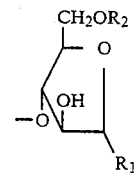

wherein R$_1$ represents:

a functional group selected notably from among aldehyde, alcohol or carboxylic acid groups or their derivatives, notably acetals, amides, ethers, esters or corresponding salts, and R$_2$ a hydrogen atom or an SO$_3^-$ group.

In an advantageous aspect of the invention, R$_1$ is constituted by an aldehyde, carboxylic acid or alcohol group.

Preferred compositions according to the invention are characterized by YW/USP ratios of the order of 10 or higher, with a Yin-Wessler activity higher than 200 IU/mg, advantageously higher than 250 IU/mg.

Preferably again, the compositions according to the invention are constituted by a major part of species of molecular weight from about 2,000 to 8,000 daltons, which corresponds to structures having from 8 to 40 saccharide units.

These products may be obtained by depolymerization of the heparin according to the process defined below.

To this end, heparin having a molecular weight of the order of 2,000 to 50,000 is subjected to the controlled action of a chemical agent capable of depolymerizing or fragmenting the heparinic chains, particularly by the controlled action of nitrous acid, said reaction being carried out under conditions adjusted to one another so as to enable a partial depolymerization of the starting heparinic material until the obtaining of a mixture formed for the most part of products having Yin-Wessler and USP titers, in a ratio higher than 2, notably at least 3, advantageously higher than 6, even higher than 10, an anti-Xa activity (Yin-Wessler) of the order of at least 200 UI/mg including end reducing groups of 2,5-anhydro-D-mannose structure:

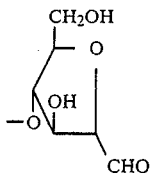

These end groups result from the action of nitrous acid at the level of the N-sulfo glucosamine units of heparin.

The depolymerization of heparin can also advantageously be carried out so as to obtain a composition formed from molecular species of which the major part, advantageously more than 80% by weight, with respect to the initial heparin, is soluble in a water-alcohol medium (water-ethanol) having a titer of 55°–62° GL, preferably of the order of 58° GL. The depolymerization conditions can also be adjusted with respect to the molecular weight of the major part of the species present in the depolymerization mixture. These conditions will then be fixed in order to obtain a majority of species of molecular weight of about 2000 to 8000 daltons (especially from 3000 to 5000 daltons), which corresponds to structures formed from 8 to 40 saccharide units.

When the desired degree of depolymerization is reached, the MPS which are precipitatable from the depolymerization mixture by an alcoholic solvent are separated and they are collected.

Advantageously, it is MPS which constitue in a way an "improved" heparin. They possess, in fact, valuable biological properties, in particular a USP titer weaker than that of the starting heparin whereas the initial Yin-Wessler activity present in the heparin is preserved, if not increased.

In addition, advantageously, the method of the invention can be applied with a heparin of pharmaceutical quality, such as commercially available, this heparin being formed from a majority of species which are insoluble in a water-alcohol medium having a titer of 55–61 GL, preferably 58 GL.

By carrying out the partial depolymerization as indicated above, heparin chains are recovered having more selective biological properties. Generally, this recovery of active chains is effected with high yields, up to 80% or more with respect to the amount of heparin processed.

This mixture of active chains can be used as such, after having undergone, taking into account the therapeutical applications envisaged, conventional purification operations such as dialysis, contacting with ion exchange resins, in particular chromatographic operations.

The heparin applied is subjected to the action of a chemical agent capable, under the controlled conditions used, of partially depolymerizing the heparin leading to biologically active chains such as mentioned above.

Recourse is more especially had to nitrous acid and $HNO_2$. This acid acts at the level of the N-sulfate glucosamine units of the heparin and converts them into units of 2,5-anhydro-D-mannose structure. Advantageously, the nitrous acid is produced in situ by the addition, in controlled amounts, of an acid of a derivative of nitrous acid, in particular a salt or an ether salt. In an advantageous embodiment of the invention, an alkali or alkaline earth salt is used, more particularly sodium nitrite $NaNO_2$. To generate the nitrous acid in situ, controlled amounts of an acid are added including, preferably, physiologically compatible anions, such as acetic acid or again hydrochloric acid.

The action of nitrous acid on heparin is advantageously carried out in an aqueous medium.

The exploitation of these features has a very particular interest with respect to the biological application envisaged.

The aqueous medium in which the depolymerization is carried out constitutes, in fact, a physiologically acceptable medium, which permits any problem relating to the removal of a solvent troublesome for said application to be avoided. In addition the salt which is formed in the medium on the production of nitrous acid is a water soluble salt, namely, sodium chloride, whose presence does not appear to be troublesome either. The subsequent purification steps of the depolymerization mixture mentioned above are thereby facilitated, no compound or organic species being introduced into the reaction medium.

According to an additional feature, advantageously applied in order to provide a mixture of MPS possessing terminal groups of greater stability, the mixture previously obtained is subjected to a treatment enabling the transformation of the aldehyde group into a more stable functional group, notably into an acid or alcohol group.

In a preferred embodiment of the invention, there is advantageously applied as raw-material a heparin possessing a molecular weight of about 2,000 to 50,000.

It may be an injectable heparin of conventional pharmaceutical quality, or a crude heparin such as obtained from extraction operations for this active principle from tissues or organs of mammifers, notably from intestinal mucus or from lungs, for example from swine or cattle. It may again be constituted by the fractions which are normally discarded during the purification of a heparin for obtaining a heparin of injectable quality and of higher specific activity.

The various parameters which come into play during a chemical reaction, in particular the concentrations of reagents, the duration, the temperature and the pH, are adjusted to one another in order to obtain the desired fractions under the most satisfactory experimental conditions.

It is known, in this respect, how these different parameters are generally closely linked.

It is clear that the modification of one of these factors can result in an adjustment of one or of several other factors in consequence.

Study of these experimental conditions by the inventors has shown that it is adventageous to apply the reagents in amounts leading to a final concentration of heparin of the order of 1 to 10 g preferably, from 1.5 to 5 g, notably close to 2 g per 100 ml of reaction medium, and the final concentration of sodium nitrite can vary from about 0.02M to 0.1M and is preferably of the order of 0.05M. The hydrochloric acid is used in a sufficient amount to obtain a pH in the reaction medium of the order of 2 to 3, advantageously from 2.2 to 2.7, preferably 2.5.

By operating at a temperature of the order of 0° to 10° C., preferably of the order of 4° C., it is left to react for a sufficient time to obtain the desired degree of depolymerization. By way of indication, an incubation of about 10 min. has appeared sufficient when operating at 4° C.

The depolymerization operation is then interrupted.

To this end, an increase in the pH of the medium is advantageously resorted to.

The addition of an alkaline agent, for example, soda, in a sufficient amount to obtain a pH at least neutral or slightly alkaline, enables the desired interruption of the depolymerization reaction to be produced.

Those mucopolysaccharides which precipitate with an alcoholic solvent are then separated.

The use of absolute ethanol, in the proportion of about 5 volumes, enables the desired separation to be obtained.

The precipitate is recovered and, for its utilisation, washed and dried.

By applying the above-indicated features, MPS fractions possessing YW/USP titers in a ratio of the order of 10/1 are isolated and having a YW activity titer higher than 200 IU/mg and this, from starting heparins having YW/USP ratios of the order of 1.

According to an additional feature, the aldehyde functions of the reducing terminal groups are converted into more stable functional groups such as alcohols or acids, which leads to MPS chains terminated for the most part by 2,5-anhydro-D-mannitol or 2,5-anhydro-D-mannonic acid structural units.

To convert the terminal 2,5-anhydro-D-mannose groups into 2,5-anhydro-D-mannitol groups, the preceding products collected from the precipitate are subjected to the action of a reducing agent by applying conditions enabling the desired transformation to be achieved at least in part.

The reducing agent is selected from among those used usually for the conversion of adhehydes into alcohol groups. Among these agents, it appears advantageous to apply a metal borohydride.

The reaction is advantageously carried out in an aqueous medium in the presence of sodium or potassium borohydride for several hours.

By operating at ambient temperature, preferably with stirring, it appears sufficient to leave the mixture to react for about 4 hours. An increase in the pH of the reaction medium is observed. This pH can reach a value of the order of 10 in the case of the use of $NaBH_4$ where a release of sodium hydroxide is observed.

In order to destroy the unreacted borohydride, the pH is lowered by the addition of acid.

In the particular case concerned, it appears advantageous to lower the pH to 4 by the addition, for example, of acetic acid.

The pH is readjusted to a value in the neighbourhood of neutrality, in particular of the order of 7.5 by the addition of an alkaline agent, for example soda.

The products which can be precipitated by alcohol are recovered from the reaction medium and the precipitate obtained is collected. This precipitate includes the desired products which the 2,5-anhydro-D-mannose end structure has been converted into a 2,5-anhydro-D-mannitol structure.

The precipitation concerned may be effected by the addition of absolute ethyl alcohol, advantageously in the proportion of 5 volumes.

To isolate the desired reduced products, a centrifugation advantageously follows and the centrifugation sediment collected which is then, if desired, washed and dried.

The study of these MPS so-obtained shows that they possess YW/USP titers in a ratio of the order of 10 or higher, with YW activity titers higher than 200 IU/mg, advantageously higher than 250 IU/mg.

Alternatively, the 2,5-anhydro-D-mannose groups are converted into 2-anhydro-D-mannonic acid groups.

The products having terminal 2,5-anhydro-D-mannose groups are reacted under the conditions necessary to obtain the desired transformation with an oxidizing agent selected from among those customarily used for the conversion of aldehyde groups into carboxylic acid groups, in particular permanganates.

The reaction is advantageously carried out in an aqueous medium at a pH higher than neutrality.

Oxidation of the aldehyde groups to acid groups results in a drop in the pH which it is advantageous to adjust constantly in the course of the reaction.

By operating at room temperature, the desired oxidation is obtained at the end of about 15 hours. The precipitated products are recovered from the reaction mixture with an alcoholic solvent.

The precipitate is then advantageously washed and dried.

It is understood that the indications of molecular weights which have been given above (and those which follow, notably in the examples) are derived from retention time measurement of solutions having pre-determined content of the material studied, in gel-permeation experiments through a gel column, under elution conditions which are also pre-determined, the logarithms of these indications of molecular weight being in the same relationship of proportionality with respect to the above-mentioned measured retention times, as are those of the molecular weights of 4,000, 6,500, 16,000 and 31,000 respectively, of sodium polystyrene-sulfonate standards, notably those marketed by the Company named CHROMPACK (Orsay-les-Ulis, France), with respect to their respective retention times measured by an identical system and under identical gel-permeation conditions.

To the extent that the treated fractions, whatever the degree of purification reaches, are in the state of salts of a physiologically acceptable metal, such as sodium, they can then be converted into mixed or simple salts containing another physiologically acceptable metal, such as calcium, by any process applicable to heparin salts. Advantageously, recourse can be had to the process described in French Pat. No. 73 13580 filed Apr. 13, 1973 by Applicant. It is recalled that this process consists essentially, starting, for example, from a sodium heparin salts, of contacting the latter with a different salt of another physiologically acceptable metal, for example calcium chloride, in a solution, then following with the separation of the metallic ions not bound to the heparin (for example by alcoholic precipitation or dialysis) and, to the extent that the substitution degree reached is not sufficient, recontacting, in a solution, the mixed heparin salt obtained at the end of the first contacting, with a further dose of the other salt, notably calcium chloride, according to the desired final substitution degree.

Other characteristics and advantages of the invention will appear from the description of the examples which follow.

EXAMPLE I

Partial depolymerization of heparin and production of a mixture of MPS having Yin-Wessler activities of at least 240 iu/mg, a ratio of their YW titer to their USP titer of at least 14 and terminal reducing groups having the structure of 2,5-anhydro-D-mannose, namely:

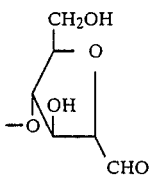

the primary hydroxyl group at the 6 positions being variously substitutable notably by an $SO_3$ group.

A heparin raw material is advantageously subjected to the controlled action of $HNO_2$, by proceeding as follows.

60 g of commercial heparin having a YW/USP ratio close to 1 and a USP titer of 160 IU/mg are dissolved in 3 l of distilled water at $+4°$ C.

Sodium nitrite $NaNO_2$ is added in a sufficient amount to have a 0.05M solution, namely 10.35 g then, the pH is adjusted to 2.5 by means of pure hydrochloric acid and it is stirred at $+4°$ C. for 10 min. The pH is then adjusted to 7.5 by means of 5N sodium hydroxide.

By the addition of 5 volumes of pure ethanol (namely 15,500 ml), the reaction products are precipitated. The precipitate formed is recovered by centrifugation. It is washed with ethanol and dried at 60° C. under high vacuum, 60 g of product having the following characteristics are collected:

| USP titer | 17 IU/mg |
|---|---|
| YW Titer | 240 IU/mg |
| AP TT(+) titer | 12 IU/mg |

(+) abbreviation of the English expressions "activated partial thromboplastin time". (equivalent to the kaolin cephaline time—of Caen J. et al. L'Hémostase, expansion scientifique 1976, p. 169-170).

In another test, procedure was as indicated above, but as starting material another heparin batch was used titrating 165 IU/mg in USP units and having a YW-/USP ratio of the order of 1.

3 g of it was dissolved in 150 ml of distilled water, at $+4°$ C., 517 mg of $NaNO_2$ then being added to the reaction medium.

At the end of the treatment carried out as previously described, 2.8 g of product having a USP titer of 24 IU/mg and a Y & W activity titer of 250 IU/mg were then recovered.

According to yet another test, carried out under the above-defined conditions, 50 g of heparin of USP titer 158 IU/mg with a YW/USP ratio close to 1 was utilised.

It was dissolved in 2,500 ml of distilled water and at $+4°$ C., 8.625 g of $NaNO_2$ was added. At the end of the treatment, 46 g of product was recovered having the following properties:

| USP titer | 13 IU/mg |
|---|---|
| Y & W activity titer | 270 IU/mg |
| APTT titer | 7 IU/mg |

EXAMPLE II

Partial depolymerization of heparin and production of MPS chains having Yin-Wessler activities of 250 iu/mg, a ratio of their YW titer to USP of 15 and terminal groups with the 2,5-anhydro-D-mannitol structure namely:

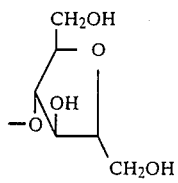

the primary alcohol at the 6 position being substitutable as explained above.

47 g of the product obtained in Example 1 were dissolved in 1200 ml of distilled water at room temperature. With vigorous stirring, 7 g of potassium borohydride $KBH_4$ was added. This stirring was kept up for 2 hours at room temperature: acetic acid was added to the reaction medium in order to lower the pH to 4.0 and thus destroy the unconsumed $KBH_4$.

The medium was subjected to stirring for 30 min, then the pH adjusted to 7.5 with 5N sodium hydroxide.

5 volumes of alcohol were added to the reaction medium.

The precipitated formed was collected, drained, washed with pure ethanol and dried under vacuum at 60° C.

46.5 g of product was recovered having the following characteristics:

| USP titer | 17 IU/mg |
|---|---|
| Y & W activity titer | 250 IU/mg |
| APTT titer | 11 IU/mg |

EXAMPLE III

Partial depolymerization of heparin and production of an MPS mixture having Yin-Wessler activities of 270 iu/mg, a ratio of their YW titer to their USP titer of 22 and terminal groups having the 2,5 anhydro-D-mannitol structure, namely

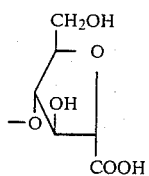

the primary hydroxyl group at the 6 position being substitutable as already indicated.

40 g of the product obtained according to the last experiment reported in Example I were dissolved in 400 ml of distilled water, at ambient temperature.

The pH was adjusted to 8.5 with 5N sodium hydroxyde; then 2 g of potassium permanganate $KMnO_4$ dissolved in 40 ml of water was added.

The reaction mixture was subjected to vigorous stirring for 15 hours. During this stirring, the pH of the mixture was constantly adjusted to 8.5 with 5N sodium hydroxide.

After 15 hours, 0.2 volume of alcohol (90 ml) was added to reduce the unreacted $KMnO_4$.

The reaction mixture was left standing for one hour. The precipitate of $MnO_2$ formed was removed by centrifugation. By precipitation with ethanol, the reaction products were recovered, they were washed and dried. In this way 35 g of product having the following properties were collected:

| | |
|---|---|
| USP titer | 12 IU/mg |
| Y & W activity titer | 270 IU/mg |
| APTT titer | 8 IU/mg. |

The products obtained according to the invention may be used in all forms of therapeutically useful salts, especially physiologically acceptable metals (sodium, calcium, magnesium or mixed salts). If necessary one may be converted to the other by the process described in French Patent Application 73-13 580 filed Apr. 13, 1973, in name of Applicant.

Pharmacological study of the products of the invention has shown that they possess distinctly more selective action, notably at the level of inhibition of factor Xa, than that of heparin.

Furthermore said products have the advantage not to account for platelet aggregation for patients for whom heparin is responsible for such a reaction.

As an indication, below are reported the results attained by testing the products of the invention in various systems.

1. Their activity with respect to platelets has been studied in vitro on human blood. If has been observed that with doses equilvalent to those of heparin, said products have the advantage not to account platelet aggregation of the blood of patients aggregation of the blood of patients for whom heparin is responsible of such a reaction.

2. The bleeding time of animals treated by product of the invention has been compared with the one obtained with heparin.

For this purpose a wound is made on the abdomen of rats, previously anaesthetized and shaved. The crack is made by pulling up a bit of skin and is recovered with a gauze during 10 min. The blood is then extracted with distilled water and the amount of haemoglobin is measured by a spectrophotometric method. The results are expressed in percentage with respect to the amount haemoglobin extracted with an animal to which a placebo has been administered.

When 5 to 10 mg/kg of products of the invention are administered, the amount of haemoglobin recovered is 130% compared to that with the placebo, while these doses of heparin of 1.2 and 4 mg/kg, percentages of 170, 180 and 325% are respectively obtained.

3. Lastly the antithrombotic activity in vivo has been studied on rabbits, using the Wessler's model: 20 u/kg of a concentrated prothrombin complex (Konyne of Cutter Laboratory) have been administered to the rabbits, and then 0.5 ml of venom of a Russel viper to cause thrombin to be formed. The activity of the products of the invention has been studied and compared to heparin, and administered 15 min. before injecting the thrombogenic products. The results are as follows:

| Doses | Heparin | Products of the invention |
|---|---|---|
| 500 μ.Y & W/kg | complete protection | complete protection |
| 250 μ.Y & W/kg | complete protection | complete protection |
| 125 μ.Y & W/kg | partial protection | partial protection |
| 62.5 μ.Y & W/kg | no protection | weak protection. |

It is hence observed in view of the results of these tests that the products of the invention possess an antithrombotic activity at least equivalent to that of heparin and advantageously exert a smaller reaction with respect to the platelets and enable the bleeding time to be reduced. These results therefore establish that the products of the invention exert a very slight action on the overall anti-coagulant activity but are endowed with antithrombotic activity of great interest.

Advantageously the products of the invention are free of toxicity.

The administration of 10 000 u/kg (Yin-Wessler titer), for example, of the products according to Example I does not cause in the rabbit any toxic reaction, nor pyrogenic effect in the pyrogenicity test in the rabbit according to the French pharmacopen.

The invention hence relates to pharmaceutical preparations which include said MPS compositions having especially an activity of at least 200 iu/mg, and a YW-/USP ratio higher than 6.

It relates more particularly to pharmaceutical preparations devoid of pyrogenic substances when necessary and containing an effective amount of active principles in association with pharmaceutical excipients.

In particular, it relates to compositions in which the pharmaceutical vehicle is suitable for oral administration. Suitable administrative forms of the invention for oral use can advantageously be gastroresistant capsules, compresses or tablets or pills.

Other pharmaceutical compositions comprise these MPS compositions in association with suitable excipients for administration rectally. Corresponding administrative forms are constituted by suppositories.

Other administrative forms are constituted by aerosols or ointments.

The invention relates also to sterile or sterilizable injectable compositions.

These solutions advantageously include 1000 to 100 000 u(Yin-Wessler)/ml of products of the invention, preferably from 5000 to 50 000, for example 25 000 u/ml, when these solutions are used for injection subcutaneously. They can contain, for example, from 500 to 10 000, especially 5000 u/ml of MPS compositions when they are intented for injection intravenously or by perfusion.

Advantageously, such pharmaceutical preparations are offered in the form of ready-for-use discardable syringes.

The invention also relates to pharmaceutical compositions containing said MPS compositions in association with another active principle, useful in particular for prophylaxis and treatment of thrombosis, such as a veinotonic agent such as dihydroergotamine, a nicotinic acid salt or a thrombolytic agent such as urokinase.

The pharmaceutical compositions according to the invention are particularly adapted to the control (preventive or curative) of certain stages of blood coagulation in man or in animals, notably in those cases where the host is subject to hypercoagulability risks, and particularly those resulting from liberation by the organism of thromboplastin, for example of tissular thromboplastin (surgical operations, atheromatous processes, development of tumors, disturbances of the mechanisms of coagulation by bacterial or enzymatic activators, etc . . . ). In order to illustrate the invention, there will be indicated below, an example of a posology which can be used in man: this posology comprises, for example, administration to the patient of 1,000 to 25,000 IU by the subcutanous route, twice or thrice per day, according to the level of the hypercoagulation risks or the thrombotic state of the patient, or from 1,000 to 25,000 IU for 24 hours by the intravenous route, in discontinuous administration at regular intervals or continuously by perfusion, or again of 1,000 to 25,000 IU (three times per week) by the intramuscular route (titers expressed in Yin-Wessler IU). The doses can, in each patient, be standardised or adjusted according to the results of previously effected blood analyses, the nature of the disease from which the patient suffers and, generally, his state of health.

The invention also relates again to the application of the mucopolysaccharides according to the invention to the constitution of biological reagents useful in the laboratory, notably as a reference standards for study of other products whose anticoagulant activity is under test, notably at the level of inhibition of the Xa factor.

We claim:

1. A process for making mucopolysaccharide heparinic fractions which have the L-iduronosyl-2-O-sulfate-(1-alpha-4)-N-sulfo-D-glucosamine-6-O-sulfate disaccharide structural units of heparin with the O-sulfated iduronic component of heparin, which mucopolysaccharide heparinic fractions do not differ from heparin with respect to the unsulfated iduronic acid component and are further defined by having a terminal structure as follows

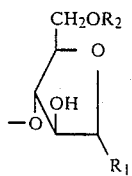

wherein $R_1$ is selected from the group consisting of aldehyde, alcohol or carboxylic acid and $R_2$ is selected from the group consisting of hydrogen or $-SO_3$, said mucopolysaccharides having a high and improved antithrombotic activity (as measured by anti-Xa activity determined by the Yin-Wessler test (YW)) as compared to heparin, and a YW/USP ratio of at least 2, which comprises the steps of partially depolymerizing heparinic chains having a molecular weight in the range of about 2,000 to about 50,000 daltons by contacting said heparinic chains with nitrous acid in an aqueous medium at a temperature in the range from about 0° C. to about ambient temperature, discontinuing the depolymerization when the mucopolysaccharides has reached a molecular weight in the range of about 2,000 to about 8,000 daltons and separating the mucopolysaccharides having said terminal structure and which do not differ from heparin with respect to the amount of the unsulfated iduronic acid component.

2. The process of claim 1 wherein the depolymerization is carried out at a pH in the range of about 2 to 3.

3. The process of claim 1 wherein the depolymerization is stopped by adjusting the pH to a pH outside the depolymerization range.

4. The process of claim 3 wherein the depolymerization is stopped by adjusting the pH to an alkaline pH.

5. The process of claim 1 wherein the nitrous acid is generated in situ from a derivative selected from the group consisting of a salt or an ether salt.

6. The process of claim 5 wherein the salt is an alkaline earth salt.

7. The process of claim 6 wherein the alkaline salt is sodium nitrite.

8. The process of claim 5 wherein the nitrous acid is generated by the addition of an acid which has a physiologically acceptable anion.

9. The process of claim 8 wherein the acid is hydrochloric acid.

10. The process of claim 5 wherein the final concentration of heparin is from about 1 to about 10 g per 100 ml of reaction medium and the concentration of sodium nitrite is from about 0.02M to 0.1M.

11. The process of claim 10 wherein the concentration of heparin is about 2 g per 100 ml of reaction medium and the concentration of sodium nitrite is about 0.05M.

12. The process of claim 5 wherein the reaction is carried out at a temperature of from about 0° C. to about 10° C.

13. The process of claim 3 wherein the pH is increased to about 7.5.

14. The process of claim 4 wherein the pH is adjusted to an alkaline pH with an alkaline agent which is sodium hydroxide.

15. The process of claim 1 wherein alcohol is added in a proportion of about at least 5 volumes with respect to the volume of the reaction medium to separate the mucopolysaccharide fractions.

16. A process according to claim 1 which further comprises reducing the recovered polysaccharide fragments recovering polysaccharide fragments having terminal structures which are 2,5-anhydro-D-mannitol groups.

17. The process of claim 16 wherein the reducing agent is potassium borohydride.

18. A process according to claim 1 which further comprises oxidizing the recovered polysaccharide fragments recovering polysaccharide fragments having terminal structures which are 2,5-anhydro-D-mannonic acid groups and their pharmaceutically acceptable salts.

19. The process of claim 18 wherein the oxidizing agent is potassium permanganate.

20. Mucopolysaccharide heparinic fractions which have the L-iduronosyl-2-O-sulfate-(1-alpha-4)-N-sulfo- D-glucosamine-6-O-sulfate disaccharide structural units of heparin with the O-sulfated iduronic component of heparin, which mucopolysaccharide heparinic fractions do not differ from heparin with respect to the unsulfated iduronic acid component and are further defined by having a terminal structure as follows

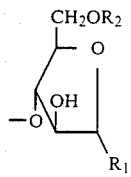

wherein $R_1$ is selected from the groups consisting of an alcohol and a carboxylic acid and $R_2$ is selected from the group consisting of hydrogen or $-SO_3$, which fractions have a molecular weight in the range of about 2,000 to 8,000 daltons and the physiologically acceptable salts thereof.

21. The mucopolysaccharide heparinic fractions of claim 20 wherein fractions have $R_2$ which is $-SO_3$ and $R_1$ is selected from the specified groups.

22. The mucopolysaccharide haparinic fractions of claim 21 wherein fractions have $R_2$ which is $-SO_3$ and $R_1$ is an aldehyde radical.

23. The mucopolysaccharide heparinic fractions of claim 21 wherein fractions have $R_2$ which is $-SO_3$ and $R_1$ is $-CH_2OH$.

24. The mucopolysaccharide heparinic fractions of claim 21 wherein $R_1$ is $-CH_2OH$ and $R_2$ is $-SO_3$.

25. The mucopolysaccharide heparinic fractions of claim 20 wherein the molecular weight is in the range of about 3,000 to about 5,000 daltons.

26. The mucopolysaccharide heparinic fractions of claim 20 which is soluble in a water-ethanol medium having a titer of 55°-61° GL.

27. The mucopolysaccharide heparinic fractions of claim 20 which have a Yin-Wessler titer higher than that of heparin and of at least 200 IU/mg and a Yin-Wessler to USP titer ratio of at least 10.

28. The mucopolysaccharide heparinic fractions of claim 20 wherein the Yin-Wessler titer is at least 250 IU/mg and the ratio of YW to USP titer is about 22.

29. The mucopolysaccharide heparinic fractions of claim 21 which is soluble in a water-ethanol medium having a titer of 55°-61° GL.

30. The mucopolysaccharide heparinic fractions of claim 21 wherein fractions have the terminal structure, 2,5-anhydro-D-mannose.

31. The mucopolysaccharide heparinic fractions of claim 21 wherein fractions have the terminal structure, 2,5-anhydro-D-mannitol.

32. The mucopolysaccharide heparinic fractions of claim 21 wherein fractions have the terminal structure, 2,5-anhydro-D-mannonic acid.

33. The mucopolysaccharide heparinic fractions of claim 21 wherein fractions have a Yin-Wessler activity from about 200 IU/mg to about 270 IU/mg.

34. Partially depolymerized heparin products having fragments which have a 2,5-anhydro-D-mannose terminal structure and a $-SO_3$ primary alcohol function in the 6-position, which products have a Yin-Wessler activity from about 200 IU/mg to about 270 IU/mg.

35. The partially depolymerized heparin products of claim 34 which have a YW/USP ratio in the range of about 10 to about 22.

36. Partially depolymerized heparin products having fragments which have a 2,5-anhydro-D-mannitol terminal structure and a $-SO_3$ primary alcohol function in the 6-position, which products have a Yin-Wessler activity from about 200 IU/mg to about 270 IU/mg.

37. Partially depolymerized heparin products having fragments which have a 2,5-anhydro-D-mannoic acid terminal structure and a $-SO_3$ primary alcohol function in the 6-position, which products have a Yin-Wessler activity from about 200 IU/mg to about 270 IU/mg.

38. The mucopolysaccharide heparinic fractions of claims 34, 36, or 37 which is soluble in a water-ethanol medium having a titer of 55°-61° GL.

39. A biological composition which has antithrombotic activity higher than that of heparin (as measured by the Yin-Wessler test) which has increased selective inhibition of the Xa factor in vitro and in vivo, which composition comprises a therapeutically acceptable carrier and in a therapeutically effective amount, a mucopolysaccharide of claims 20, 21, 22, 23, 24, 25, 26, 27, 28 29, 30, 31, 32, 33, 34, 35, 36, 37 or 41.

40. A therapeutic method for controlling thrombosis in a patient which comprises administering to said patient a biological composition of claim 39 and controlling thrombosis by inhibiting coagulation factor Xa.

41. The mucopolysaccharide heparinic fractions of claim 20 which have a ratio of anti-Xa to USP titers of at least 6.

42. The mucopolysaccharide fractions of claim 20 which have an anti-Xa titer of over about 22 units/mg and a ratio of titers of anti-Xa to USP of at least 3.

* * * * *

UNITED STATES PATENT AND TRADEMARK OFFICE
CERTIFICATE OF CORRECTION

PATENT NO. : 4,500,519
DATED : February 19, 1985
INVENTOR(S) : Lormeau et al

It is certified that error appears in the above-indentified patent and that said Letters Patent is hereby corrected as shown below:

On the title page : Item [30]

Under Foreign Application Priority Data on the first page of the patent, delete

"Mar. 20, 1980   [FR]   France....78 31357"

and replace with

--Nov. 6, 1978   [FR]   France....78 31357
  Jul. 20, 1979  [FR]   France....79 18873
  Mar. 20, 1980  [FR]   France....80 06282

Signed and Sealed this

Fourth Day of April, 1995

Attest:

BRUCE LEHMAN

*Attesting Officer*          *Commissioner of Patents and Trademarks*